United States Patent
Hyogo et al.

(10) Patent No.: US 9,717,623 B2
(45) Date of Patent: Aug. 1, 2017

(54) APPARATUS FOR CONTROLLING BODY TEMPERATURE AND METHOD THEREOF

(71) Applicant: NIHON KOHDEN CORPORATION, Tokyo (JP)

(72) Inventors: Mitsushi Hyogo, Tokyo (JP); Takayuki Mogi, Tokyo (JP); Yoshihiro Takayanagi, Tokyo (JP); Masahiro Echigo, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 331 days.

(21) Appl. No.: 14/606,594

(22) Filed: Jan. 27, 2015

(65) Prior Publication Data

US 2015/0209175 A1    Jul. 30, 2015

(30) Foreign Application Priority Data

Jan. 27, 2014    (JP) .................. 2014-012691

(51) Int. Cl.
*A61F 7/00*    (2006.01)
*A61F 7/02*    (2006.01)

(52) U.S. Cl.
CPC ........ *A61F 7/02* (2013.01); *A61F 2007/0018* (2013.01); *A61F 2007/0055* (2013.01); *A61F 2007/0056* (2013.01); *A61F 2007/0086* (2013.01); *A61F 2007/0095* (2013.01); *A61F 2007/0298* (2013.01)

(58) Field of Classification Search
CPC .............................................. A61F 2007/0298
See application file for complete search history.

(56) References Cited

U.S. PATENT DOCUMENTS

| | | | |
|---|---|---|---|
| 6,969,399 B2 | 11/2005 | Schock et al. | |
| 7,303,579 B2 | 12/2007 | Schock et al. | |
| 7,377,935 B2 | 5/2008 | Schock et al. | |
| 7,547,320 B2 | 6/2009 | Schook et al. | |
| 7,631,377 B1 * | 12/2009 | Sanford | A47C 21/044 5/413 R |
| 7,666,213 B2 | 2/2010 | Freedman, Jr. et al. | |
| 7,731,739 B2 | 6/2010 | Schock et al. | |
| 7,771,461 B2 | 8/2010 | Schock et al. | |
| 7,892,271 B2 | 2/2011 | Schock et al. | |
| 8,425,582 B2 | 4/2013 | Schock et al. | |
| 8,435,277 B2 | 5/2013 | Schock et al. | |
| 2003/0208251 A1 * | 11/2003 | Papay | A61F 7/00 607/107 |
| 2007/0055325 A1 * | 3/2007 | Worm | A62B 17/005 607/96 |

FOREIGN PATENT DOCUMENTS

JP    2005-532141    10/2005
WO    2004/006814    1/2004

* cited by examiner

*Primary Examiner* — Kaitlyn Smith
(74) *Attorney, Agent, or Firm* — Konomi Takeshita

(57) ABSTRACT

The present invention provides an apparatus for controlling body temperature of a patient during hypothermia treatment, comprising: a body trunk cooling unit having a first affixing portion to be applied on a surface of the trunk of a patient's body and for cooling the surface of the trunk of the patient's body; and a body peripheral part heating unit having a second affixing portion to be applied to the peripheral part of the patient's body and for heating the peripheral part of the body by utilizing exhaust heat from the body trunk cooling unit and suppressing activation of cold receptors of the skin of the patient.

14 Claims, 2 Drawing Sheets

(a)

(b)

APPARATUS FOR CONTROLLING BODY TEMPERATURE AND METHOD THEREOF

CROSS REFERENCE TO RELATED APPLICATIONS

This application claims priority under 35 U.S.C. 119 based upon Japanese Patent Application Serial No. 2014-012691, filed on Jan. 27, 2014. The entire disclosures of the aforesaid applications are incorporated herein by reference.

FIELD OF THE INVENTION

The present invention pertains to a device for regulating the body temperature of a patient during therapeutic hypothermia treatment.

BACKGROUND OF THE INVENTION

In therapeutic hypothermia treatment, the brain temperature of a patient is rapidly decreased, and the state thereof must be maintained for a prescribed period of time. In order to do so, a blanket that covers a portion of the body of the patient is utilized. For said type of blanket, a sheet which covers the body wherein flow channels for flowing liquid are formed is known (for example, refer to Japanese Laid-Open Patent Publication No. 2005-532141). By properly controlling the temperature of said liquid, heat is exchanged between said liquid and the body surface of the patient, via said sheet, and the body temperature of the patient is adjusted.

When the body surface of a patient is cooled in the abovementioned manner, cold receptors distributed throughout the skin are activated, whereby small blood vessels in the skin contract and blood flow is restricted. Heat in organisms is transmitted most efficiently by blood. However, when cutaneous blood flow is restricted, even if the body surface is cooled, heat is not readily transmitted to the center thereof, and there are cases in which regulation of brain temperature and the like are hindered.

SUMMARY OF THE INVENTION

Accordingly, the present invention aims to efficiently transmit therapeutic hypothermia treatment cooling effects on the body surface of a patient to the center of said patient.

In order to attain the above object, according to a first principal aspect of the present invention, there is provided an apparatus for controlling body temperature of a patient during hypothermia treatment, comprising: a body trunk cooling unit having a first affixing portion to be applied on a surface of the trunk of a patient's body and for cooling the surface of the trunk of the patient's body; and a body peripheral part heating unit having a second affixing portion to be applied to the peripheral part of the patient's body and for heating the peripheral part of the body by utilizing exhaust heat from the body trunk cooling unit and suppressing activation of cold receptors of the skin of the patient.

According to one embodiment of the present invention, the body peripheral part heating unit of the apparatus further comprises a flow channel for exhaust heat fluid for guiding exhaust heat fluid exhausted from the body trunk cooling unit to the second affixing portion.

According to one embodiment of the invention, the apparatus further comprises a temperature controller for controlling the temperature of the exhaust heat fluid.

According to one embodiment of the invention, the temperature controller of the apparatus comprises a temperature sensor and a cooling device, and wherein, if the temperature sensor detects that the temperature of the exhaust heat fluid exceeds a predetermined value, the exhaust heat fluid is cooled by the cooling device.

According to one embodiment of the invention, the apparatus is provided wherein the controlling of the temperature is performed by controlling mixture of the exhaust heat fluid and fluid cooled by the body trunk cooling unit.

According to one embodiment of the invention, the body trunk cooling unit of the apparatus further comprises: a fluid cooling unit for cooling fluid; a flow channel for cooled fluid for guiding cooled fluid cooled by the fluid cooling unit to the first affixing portion; an exhaust outlet for exhausting heat generated from the cooling of fluid by the fluid cooling unit.

According to one embodiment of the invention, the apparatus is provided wherein the cooled fluid and the exhaust heat fluid are air.

Furthermore, according to second principal aspect of the present invention, there is provided a method for controlling body temperature of a patient during hypothermia treatment, comprising: a step for applying a first affixing portion of a body trunk cooling unit to be applied on a surface of the trunk of a patient's body; a body trunk cooling step for cooling the surface of the trunk of the patient's body; a step for applying a second affixing portion of a body peripheral part heating unit to be applied to the peripheral part of the patient's body; and a body peripheral part heating step for heating the peripheral part of the body by utilizing exhaust heat from the body trunk cooling unit and suppressing activation of cold receptors of the skin of the patient.

According to one embodiment of the invention, the body peripheral part heating unit of the method further comprises a flow channel for exhaust heat fluid for guiding exhaust heat fluid exhausted from the body trunk cooling unit to the second affixing portion.

According to one embodiment of the invention, the method further comprises a temperature controller for controlling the temperature of the exhaust heat fluid.

According to one embodiment of the invention, the temperature controller of the method comprises a temperature sensor and a cooling device, and wherein, if the temperature sensor detects that the temperature of the exhaust heat fluid exceeds a predetermined value, the exhaust heat fluid is cooled by the cooling device.

According to one embodiment of the invention, the method is provided wherein the controlling of the temperature is performed by controlling mixture of the exhaust heat fluid and fluid cooled by the body trunk cooling unit.

According to one embodiment of the invention, the body trunk cooling unit of the method further comprises: a fluid cooling unit for cooling fluid; a flow channel for cooled fluid for guiding cooled fluid cooled by the fluid cooling unit to the first affixing portion; an exhaust outlet for exhausting heat generated from the cooling of fluid by the fluid cooling unit.

According to one embodiment of the invention, the method is provided wherein the cooled fluid and the exhaust heat fluid are air.

Other features and advantages of the present invention will become apparent from the following detailed description, taken in conjunction with the accompanying drawings, which illustrate, by way of example, the principles of the invention.

DETAILED DESCRIPTION OF THE INVENTION

Embodiments of the present invention will be explained in detail below while referring to the attached drawings. However, in each diagram used in the below explanation, the scale has been modified, as appropriate, such that each member is of a discernible size.

Figure 1:
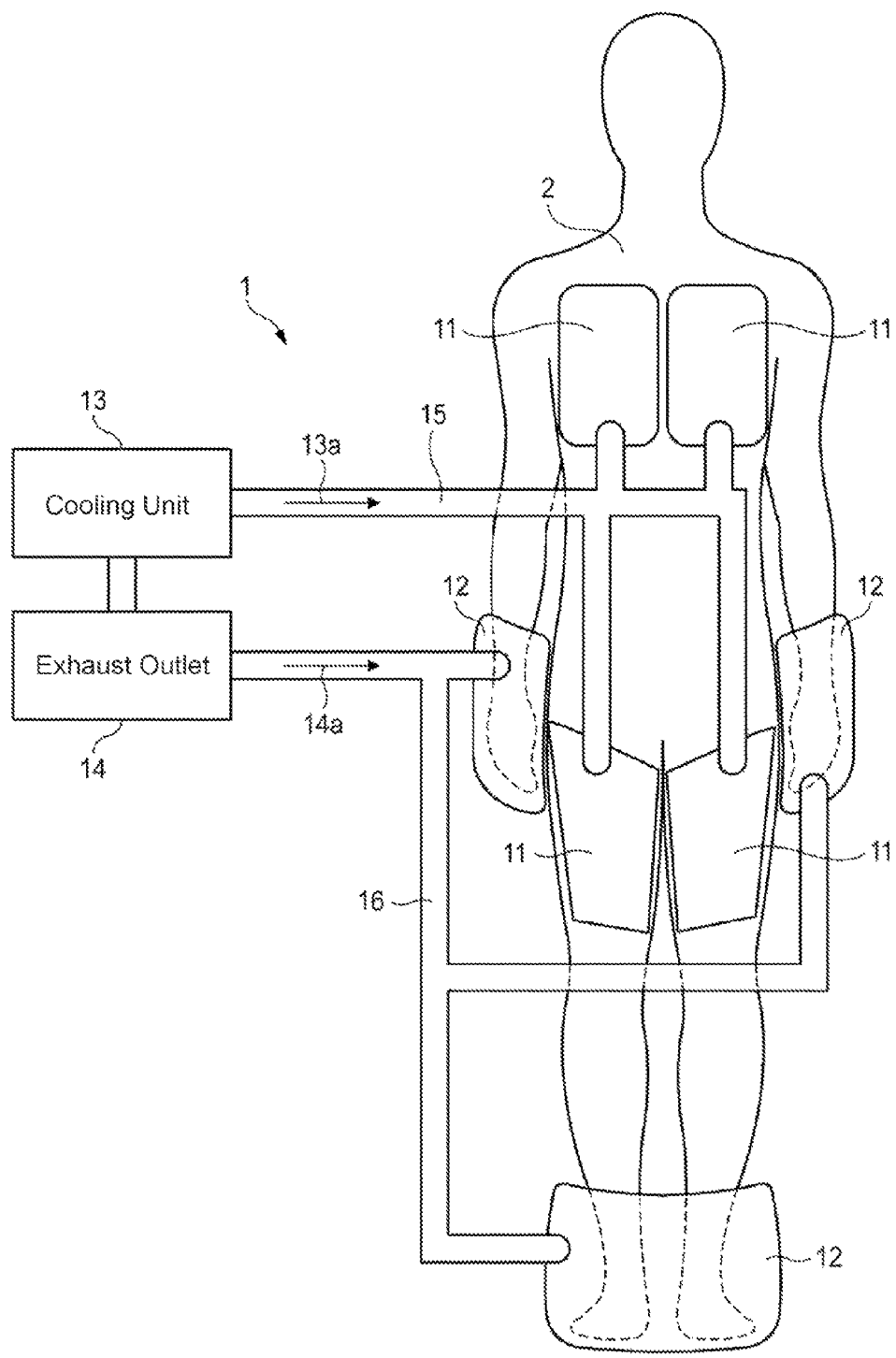
FIG. 1 is a diagram schematically representing a configuration of the body temperature regulator as in one embodiment of the present invention.

FIG. 1 is a diagram schematically representing a configuration of the body temperature regulator as in one embodiment of the present invention. The body temperature regulator is a device for regulating the body temperature of a patient (2) during therapeutic hypothermia treatment.

The body temperature regulator (1) is provided with first affixing portions (11). The first affixing portions (11) are configured so as to be affixed to the trunk of the body of the patient (2). The chest, abdomen, back, and thighs, etc., can be given as examples of the trunk of the body. The first affixing portions (11) may be in the form of pads, blankets, or sheets, etc. In the example in the drawing, a state is illustrated in which the first affixing portions (11), which are in the form of pads, are affixed to the chest and thighs of the patient (2).

The body temperature regulator (1) is provided with second affixing portions (12). The second affixing portions (12) are configured so as to be affixed to peripheral parts of the patient (2). The hands, forearms, feet, and lower extremities, etc., can be given as examples of peripheral parts. The second affixing portions (12) may be in the form of pads, blankets, sheets, or bags etc. In the example in the drawing, a state is illustrated in which the second affixing portions (12), which are in the form of bags, hold the hands and feet of a patient (2).

The body temperature regulator (1) is provided with a cooling unit (13). The cooling unit (13) is configured so as to cool a fluid to a prescribed temperature. A gas or liquid selected, as appropriate, can be given as examples of the fluid.

The body temperature regulator (1) is provided with an exhaust outlet (14). The exhaust outlet (14) is configured so as to discharge heat generated when the cooling unit (13) cools the fluid. Namely, exhaust heat air (14a) is discharged from the exhaust outlet (14).

The body temperature regulator (1) is provided with a first flow channel (15). The first flow channel (15) is configured so as to guide fluid (13a) cooled by the cooling unit (13) to the first affixing portions (11). The first flow channel (15) may be configured from a flexible hose or tube, for example, communicating between the cooling unit (13) and the first affixing portions (11). The fluid (13a) cooled by the cooling unit (13) reaches the first affixing portions (11) via the first flow channel (15), and cools the first affixing portions (11), whereby the trunk of the body of the patient (2) to which the first affixing portions (11) are affixed is cooled.

The body temperature regulator (1) is provided with a second flow channel (16). The second flow channel (16) is configured so as to guide the exhaust heat air (14a) discharged by the exhaust outlet (14) to the second affixing portions (12). The second flow channel (16) may be configured from a flexible hose or tube, for example, communicating between the exhaust outlet (14) and the second affixing portions (12). The exhaust heat air (14a) discharged by the exhaust outlet (14) reaches the second affixing portions (12) via the second flow channel (16), and heats the second affixing portions (12), whereby the peripheral parts of the patient (2) to which the second affixing portions (12) are affixed are heated.

From the abovementioned configuration, peripheral parts of a patient (2) are heated by the second affixing portions (12) while therapeutic hypothermia treatment utilizing the first affixing portions (11) is being performed, whereby activation of cold receptors in the skin is suppressed and restriction of cutaneous blood flow is suppressed. Accordingly, the cooling effects of therapeutic hypothermia treatment on the body surface of a patient are able to be efficiently transmitted to the center of the patient.

Moreover, heat generated naturally when the fluid is cooled (i.e. the first affixing portions (11) are cooled) by the cooling unit (13) is reused for the heat which heats the second affixing portions (12), whereby the efficiency of energy utilization of the entire body temperature regulator (1) can be increased. Furthermore, the configuration of the body temperature regulator (1) can be simplified and miniaturized, since separately attaching a heating device or the like is not necessary.

FIG. 2 represents one portion of a body temperature regulator (1A) according to a modification. Using the same reference numbers for components which are the same or similar to the abovementioned embodiment, redundant explanations will be omitted. The body temperature regulator (1A) is provided with a temperature controller (17). The temperature controller (17) is configured so as to adjust the temperature of the exhaust heat air (14a) discharged from the exhaust outlet (14).

Figure 2A:
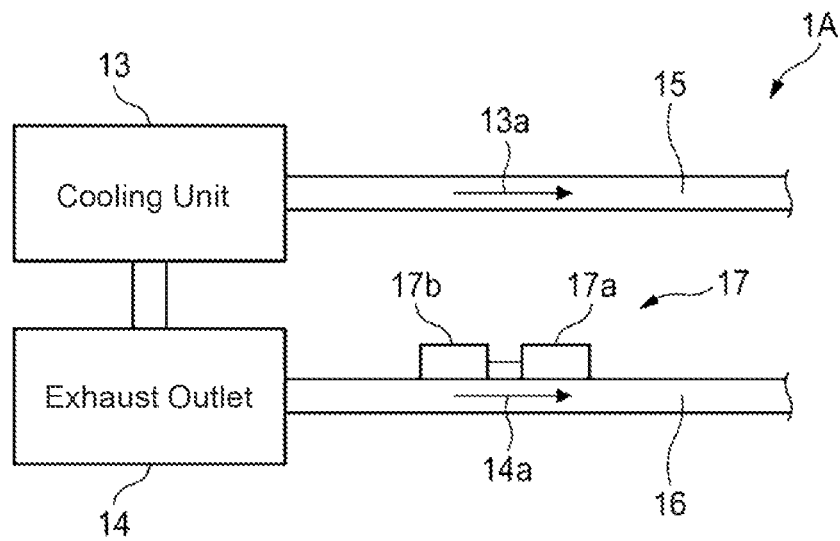
FIGS. 2A and 2B are diagrams schematically representing modifications of the body temperature regulator.

For example, as illustrated in FIG. 2A, the temperature controller (17) is configured to comprise a temperature sensor (17a) and a Peltier element (17b). The temperature sensor (17a) detects the temperature in the second flow channel (16) (i.e. the temperature of the exhaust heat air (14a)). The Peltier element (17b) is configured so as to work when the temperature detected by the temperature sensor (17a) exceeds a prescribed value. The exhaust heat air (14a) flowing within the second flow channel (16) is cooled from the Peltier element (17b) working.

From such a configuration the temperature-controlled heat exhaust air (14a) can be guided to the second affixing portions (12), whereby peripheral parts of the patient (2) can be heated at a suitable temperature by the second affixing portions (12). Accordingly, the cooling effects of therapeutic hypothermia treatment on the body surface of a patient are able to be efficiently transmitted to the center of the patient.

Figure 2B:
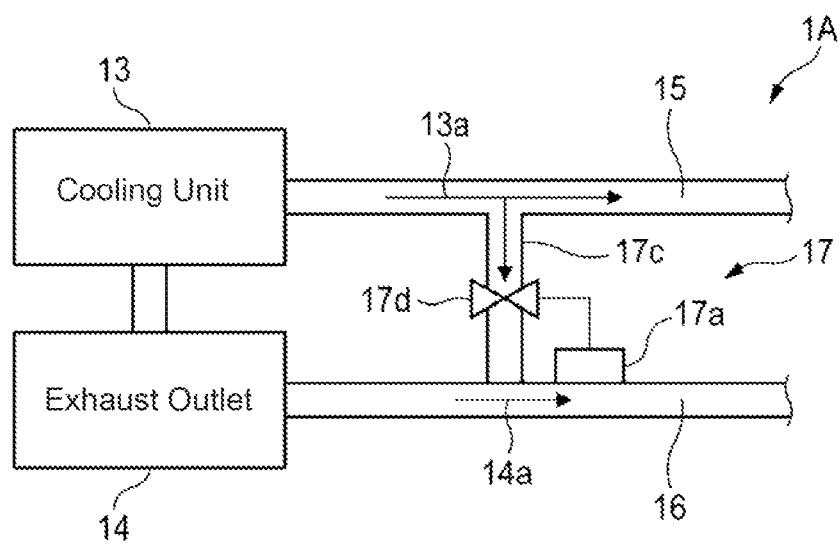

Alternatively, as illustrated in FIG. 2B, the temperature controller (17) is configured to cool the second flow channel (16) using the fluid (13a) cooled by the cooling unit (13). Specifically, the temperature controller (17) is configured to comprise a temperature sensor (17a), a branching channel (17c), and a valve (17d). The temperature sensor (17a) detects the temperature in the second flow channel (16) (i.e. the temperature of the exhaust heat air (14a)). The branching channel (17c) is formed from branching a portion of the first flow channel (15). The end of the branching channel (17c) is in contact with or contiguous with a portion of the second flow channel (16). The valve (17d) selectively switches the branching channel (17c) between an open state and a closed state.

The valve (17d) is configured so as to open the branching channel (17c) when the temperature detected by the temperature sensor (17a) exceeds a prescribed value. The fluid (13a) cooled by the cooling unit (13) is guided to the second flow channel (16) by means of the branching channel (17c) being opened, and the heat exhaust air (14a) flowing within the second flow channel (16) is cooled.

From such a configuration the temperature-controlled heat exhaust air (14a) can be guided to the second affixing portions (12). Moreover, the temperature of the heat exhaust air (14a) can be efficiently controlled using the fluid (13a) cooled by the cooling unit (13), whereby peripheral parts of the patient (2) can be heated at a suitable temperature by the second affixing portions (12). Accordingly, the cooling effects of therapeutic hypothermia treatment on the body surface of a patient are able to be efficiently transmitted to the center of the patient.

As mentioned above, the fluid (13a) cooled by the cooling unit (13) may be a gas or liquid, as appropriate. However, it is preferable for the fluid (13a) to be air.

Because it is easy to control air flow, a higher heat transference can be easily achieved with air than with liquid. With air, the trunk of the body of a patient can therefore be cooled via first affixing portions more efficiently than in cases in which liquid is used as the fluid. Accordingly, the cooling effects of therapeutic hypothermia treatment on the body surface of a patient are able to be efficiently transmitted to the center of the patient. Furthermore, by using air that can be obtained without requiring special equipment as the fluid (13a), the configuration of the body temperature regulator (1) can be simplified and miniaturized. Moreover, by using air as the fluid (13a), it is not necessary to provide equipment for preventing liquid leakage, whereby the configuration of the body temperature regulator (1) can be simplified and miniaturized.

The abovementioned embodiments are meant to facilitate comprehension of the present invention and are not meant to limit the present invention. While the present invention may, without departing from the purpose of the embodiments, be modified or improved, it is clear that equivalents of the embodiments are included in the present invention.

The form and size of the first affixing portions (11) and the second affixing portions (12) are not limited to the embodiments described above. The form and size may be selected, as appropriate, in accordance with the site on the patient requiring cooling and heating, the medical treatment, and the intended use.

In the configuration illustrated in FIG. 2B, the end of the branching channel (17c) is in contact with or contiguous with the second flow channel (16). However, the branching channel (17c) may be configured to be in communication with the second flow channel (16).

It is to be understood that the above-described embodiments are illustrative of only a few of the many possible specific embodiments which can represent applications of the principles of the invention. Numerous and varied other arrangements can be readily devised by those skilled in the art without departing from the spirit and scope of the invention.

What is claimed is:

1. An apparatus for controlling body temperature of a patient during hypothermia treatment, comprising:
    a body trunk cooling unit having a first affixing portion to be applied on a surface of the trunk of a patient's body and for cooling the surface of the trunk of the patient's body; and
    a body peripheral part heating unit having a second affixing portion to be applied to the peripheral part of the patient's body and for heating the peripheral part of the body by utilizing exhaust heat from the body trunk cooling unit and suppressing activation of cold receptors of the skin of the patient.

2. The apparatus as recited in claim 1, wherein the body peripheral part heating unit further comprises a flow channel for exhaust heat fluid for guiding exhaust heat fluid exhausted from the body trunk cooling unit to the second affixing portion.

3. The apparatus as recited in claim 2, further comprising a temperature controller for controlling the temperature of the exhaust heat fluid.

4. The apparatus as recited in claim 3, wherein the temperature controller comprises a temperature sensor and a cooling device, and wherein, if the temperature sensor detects that the temperature of the exhaust heat fluid exceeds a predetermined value, the exhaust heat fluid is cooled by the cooling device.

5. The apparatus as recited in claim 3, wherein the controlling of the temperature is performed by controlling mixture of the exhaust heat fluid and fluid cooled by the body trunk cooling unit.

6. The apparatus as recited in claim 2, wherein the body trunk cooling unit further comprises:
    a fluid cooling unit for cooling fluid;
    a flow channel for cooled fluid for guiding cooled fluid cooled by the fluid cooling unit to the first affixing portion;
    an exhaust outlet for exhausting heat generated from the cooling of fluid by the fluid cooling unit.

7. The apparatus as recited in claim 6, wherein the cooled fluid and the exhaust heat fluid are air.

8. A method for controlling body temperature of a patient during hypothermia treatment, comprising:
    applying a first affixing portion of a body trunk cooling unit to be applied on a surface of a trunk of a patient's body;
    cooling the surface of the trunk of the patient's body;
    applying a second affixing portion of a body peripheral part heating unit to be applied to a peripheral part of the patient's body; and
    heating the peripheral part of the body by utilizing exhaust heat from the body trunk cooling unit and suppressing activation of cold receptors of the skin of the patient.

9. The method as recited in claim 8, wherein the body peripheral part heating unit further comprises a flow channel for exhaust heat fluid for guiding exhaust heat fluid exhausted from the body trunk cooling unit to the second affixing portion.

10. The method as recited in claim 9, further comprising controlling the temperature of the exhaust heat fluid by a temperature controller.

11. The method as recited in claim 10, wherein the temperature controller comprises a temperature sensor and a cooling device, and wherein, if the temperature sensor detects that the temperature of the exhaust heat fluid exceeds a predetermined value, the exhaust heat fluid is cooled by the cooling device.

12. The method as recited in claim 10, wherein the controlling the temperature is performed by controlling mixture of the exhaust heat fluid and fluid cooled by the body trunk cooling unit.

13. The method as recited in claim 9, wherein the body trunk cooling unit further comprises:

a fluid cooling unit for cooling fluid;
a flow channel for cooled fluid for guiding cooled fluid cooled by the fluid cooling unit to the first affixing portion;
an exhaust outlet for exhausting heat generated from the cooling of fluid by the fluid cooling unit.

14. The method as recited in claim 13, wherein the cooled fluid and the exhaust heat fluid are air.

\* \* \* \* \*